(12) United States Patent
Bekiarian et al.

(10) Patent No.: US 9,212,193 B2
(45) Date of Patent: Dec. 15, 2015

(54) AMINE-ACCELERATED PROCESS FOR THE SURFACE TREATMENT OF COLLOIDAL SILICA AND PRODUCTS THEREOF

(75) Inventors: Paul Gregory Bekiarian, Wilmington, DE (US); Gordon Mark Cohen, Wynnewood, PA (US); Paul Douglas Stull, Wilmington, DE (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 161 days.

(21) Appl. No.: 14/004,725

(22) PCT Filed: Jun. 30, 2011

(86) PCT No.: PCT/US2011/042473
§ 371 (c)(1),
(2), (4) Date: Sep. 12, 2013

(87) PCT Pub. No.: WO2012/138365
PCT Pub. Date: Oct. 11, 2012

(65) Prior Publication Data
US 2013/0345461 A1 Dec. 26, 2013

Related U.S. Application Data

(60) Provisional application No. 61/471,863, filed on Apr. 5, 2011.

(51) Int. Cl.
| | |
|---|---|
| G07F 7/04 | (2006.01) |
| C07F 7/18 | (2006.01) |
| B82Y 30/00 | (2011.01) |
| C09C 1/30 | (2006.01) |

(52) U.S. Cl.
CPC .............. *C07F 7/1836* (2013.01); *B82Y 30/00* (2013.01); *C09C 1/3081* (2013.01); *C01P 2004/64* (2013.01)

(58) Field of Classification Search
CPC .................................................. C07F 7/1836
USPC ....................................................... 556/413
See application file for complete search history.

(56) References Cited

U.S. PATENT DOCUMENTS

| | | | |
|---|---|---|---|
| 6,528,604 | B1 | 3/2003 | Eriyama et al. |
| 8,242,204 | B2 | 8/2012 | Kwag et al. |
| 8,987,369 | B2 | 3/2015 | Bekiarian et al. |
| 2008/0087314 | A1 | 4/2008 | Xiao et al. |
| 2008/0194855 | A1 | 8/2008 | Gottschalk-Gaudig et al. |
| 2008/0216709 | A1 | 9/2008 | Steingrover et al. |
| 2013/0344338 | A1 | 12/2013 | Bekiarian et al. |

FOREIGN PATENT DOCUMENTS

| | | |
|---|---|---|
| GB | 1432014 | 4/1976 |
| JP | 2008105919 A | 5/2008 |
| WO | 2005/019195 A2 | 3/2005 |
| WO | 2007/050462 A2 | 5/2007 |
| WO | WO 2007117271 A1 * | 10/2007 |
| WO | 2008/033988 A1 | 3/2008 |
| WO | 2009/094023 A1 | 7/2009 |
| WO | 2010/059710 A1 | 5/2010 |
| WO | WO 2010059710 A1 * | 5/2010 |
| WO | 2012/138363 A1 | 10/2012 |

OTHER PUBLICATIONS

Deng et al., J. Amer. Chem. Soc. (2010), 132(24), 8466-8473.*
Guo et al., J. Materials Chem. (2002), 12(3), 468-472.*
Selected abstracts from STN search dated Mar. 30, 2015, 13 pages.*
PCT International Search Report and Written Opinion for International application No. PCT/US2011/042473, dated Dec. 19, 2011.
Non-Final Office Action, U.S. Appl. No. 14/004,695, dated Aug. 21, 2014.
PCT International Search Report and Written Opinion for International application No. PCT/US2011/042469, dated Dec. 1, 2011.
PCT International Preliminary Report on Patentability Cover Sheet for International application No. PCT/US2011/042469, dated Oct. 17, 2013.
PCT International Preliminary Report on Patentability for International application No. PCT/US2011/042469, issued Oct. 8, 2013.
Celia et al, Three steps to organic-inorganic hybrid films showing superhydrophilic properties, Soft Matter, 2011, 10057-10062, 7.
Li et al, Composite nanospheres of PAA/silica controlled by anionic polymer, Gaodeng Xuexiao Huaxue Xuebao, 2009, 2487-2490, 30(12)—Abstract.
Rostami et al, Investigating the interfacial interaction of different aminosilane treated nano silicas with a polyurethane coating, Applied Surface Science, 2010, 899-904, 257.
Scaffaro et al, Surface modification of poly(ethylene-co-acrylic acid) with amino-functionalized silica nanoparticles, Journal of Materials Chemistry, 2011, 3849-3857, 21.
Wang et al, Effect of acrylic polymer and nanocomposite with nano-SiO2 on thermal degradation and fire resistance of APP-DPER-MEL coating, Polymer Degradation and Stability, 2006, 1937-1947, 91.
Abstract of CN1654533A, Aug. 17, 2005, Nanjing University of Technology.
Abstract of CN101089055A, Dec. 19, 2007, Wuhan University of Technology.
Abstract of CN102181021A, Sep. 14, 2011, Univ North China.
Abstract of DE20041057997, Jun. 8, 2006, Wacker Chemie AG.
Abstract and English translation of JP2008105919A, May 8, 2008, Hakuto Co Ltd.

* cited by examiner

*Primary Examiner* — Porfirio Nazario Gonzalez
*Assistant Examiner* — Kofi Adzamli

(57) ABSTRACT

This invention relates to the use of certain amine promoters in processes for surface-treating colloidal silica nanoparticles with selected aromatic aminosilanes, aromatic aminoalkylsilanes, and secondary and tertiary aliphatic aminosilanes. This process provides surface-modified nanoparticle colloidal silica without causing the silica nanoparticles to gel, agglomerate, or aggregate.

14 Claims, No Drawings

AMINE-ACCELERATED PROCESS FOR THE SURFACE TREATMENT OF COLLOIDAL SILICA AND PRODUCTS THEREOF

This application claims priority to Provisional Application No. 61/471,863 filed Apr. 5, 2011 which is herein incorporated by reference.

FIELD OF THE INVENTION

This invention relates to amine-accelerated processes for surface-treating colloidal silica nanoparticles with selected silanes.

BACKGROUND

Conventional filled polymer systems often have improved modulus, stiffness, and hardness relative to unfilled polymer systems. Use of nanofillers in polymers can improve the creep-resistance, wear-resistance, and modulus of the nano-composite, without adversely affecting polymer aesthetics like clarity. Nanoparticles can also have a strong influence on the glass transition temperature (Tg) of polymers.

Although the high surface area of nanoparticles creates a large interface with host polymers, this high surface area also makes nanoparticles more prone to forming larger particles through agglomeration (a potentially reversible self-association that is frequently difficult and/or costly to reverse) or aggregation (an irreversible self-association). Agglomerated and aggregated nanoparticles frequently do not offer the level of benefits afforded by well-dispersed primary nanoparticles because they have less surface area in contact with the polymer matrix.

Colloidal silica is a potentially convenient source of nanoparticles (particles that are 100 nm in diameter or smaller) that might be blended with a polymer to improve various physical properties of the polymer. But colloidal silica can be difficult to disperse in solvents or polymers because the polar silanol groups on the surface of the nanoparticles can cause them to agglomerate. Even worse, the silanols can react chemically with each other ("condense") and form irreversible linkages that cause the particles to irreversibly aggregate.

Attempts to overcome this tendency to agglomerate have included grafting polystyrene "brushes" onto the silica nanoparticle surface, but these modified particles are useful only for blends of polymers of the same composition as the brushes, namely polystyrene. In addition, this approach uses an expensive multistep, reversible addition-fragmentation chain transfer polymerization process to modify the surface.

Silanes can also be used to modify silica surfaces like glass, glass fibers, and fumed silica (aggregates of silica nanoparticles), but are rarely used with primary, unaggregated silica particles. Phenylsilane modification improves the compatibility and dispersibility of silica nanoparticles in non-polar aromatic polymers such as polystyrene. Similarly, perfluoroalkylethylsilanes can be used for fluoropolymers.

Surface modification of colloidal silica (unaggregated silica nanoparticles suspended in a liquid medium) is not as facile as surface modification of glass or aggregated particles. The modification can adversely affect the stability of the nanoparticles and cause them to agglomerate or irreversibly aggregate, which leads to particle clusters that are not nanoparticles. This agglomeration or aggregation can also make the particles settle out or form a gel. These suspended particle clusters, settled particles, or gels cannot usually be well-dispersed in polymers.

It is possible to modify silica with a few selected silane reagents without these adverse effects. However, silane modification of silica is slow. To accelerate the surface modification reaction and increase the degree of modification of the silica particles in colloidal and non-colloidal form, heat can be employed. However, when colloidal silica nanoparticles are suspended in low-boiling solvents like 2-propanol or 2-butanone, the reactions must be carried out at elevated pressures as well, since a temperature that is sufficient to effect the modification to a sufficient degree of completion in an economical length of time is above the solvents' boiling points. While it is possible to find commercially available colloidal silica products in solvents of higher boiling point, these solvents may not be compatible with the polymer in which the particles are to be dispersed by solution blending. In solution blending, it is necessary to dissolve the particle and polymer in the same solvent, or in solvents which are miscible with each other. It may not be economical or technically feasible to transfer the silica nanoparticles from their commercially available colloids to a higher boiling point solvent that is compatible with the polymer.

When elevated temperature cannot be used, it is desirable to find a catalyst to accelerate the surface modification process. The silane modification of glass surfaces (a non-colloidal form of silica) is slow and is therefore sometimes carried out with acid catalysts, and occasionally with amine catalysts. Although catalysts can be used for modification of non-colloidal silica (e.g., glass or fumed silica), they may cause the nanoparticles in colloidal silica to agglomerate or aggregate into large clusters or to undesirably settle out of suspension or form a gel.

It has been found that aromatic aminosilanes do surface-modify colloidal silica without causing the silica nanoparticles to gel, agglomerate, or aggregate, but the reactions are very slow and can be incomplete if not carried out for a very long time. Thus, there is a need to increase the rate of this surface modification by aromatic aminosilanes for colloidal silica with nanoparticles at temperatures at or below the boiling point of the solvent in which the silica is suspended, without causing the silica nanoparticles to gel, agglomerate, or aggregate. There is also a need to increase the rate of surface modification of colloidal silica with nanoparticles by other silanes that react slowly with colloidal silica at temperatures at or below the boiling point of the solvent in which the silica is suspended.

SUMMARY

One aspect of the present invention is a process comprising forming a reaction mixture comprising:
a) a dispersion of colloidal silica nanoparticles having an average diameter of less than 75 nm;
b) a silane of Formula 1:

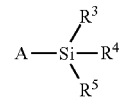

Formula 1 wherein
A is selected from the group consisting of alkyl groups, alkenyl groups, arylalkyl groups, alkoxyalkyl groups, alkoxyaryl groups, fluorine-substituted alkyl groups, aryl groups and N-aryl-substituted aminoalkyl groups;

$R^3$ is a $C_1$-$C_{10}$ alkoxy group; and
$R^4$ and $R^5$ are independently selected from the group consisting of $C_1$-$C_{10}$ alkyl and $C_1$-$C_{10}$ alkoxy groups; and
c) an amine promoter having a $pK_b$ less than about 7.0.

DETAILED DESCRIPTION

It has been found that the use of certain aromatic aminosilanes, aromatic aminoalkylsilanes, and secondary and tertiary aliphatic aminosilanes allows one to surface-modify nanoparticle colloidal silica without causing the silica nanoparticles to gel, agglomerate, or aggregate. It has also been found that amine promoters can accelerate this surface-modification reaction.

The aminosilanes can also be used in conjunction with other silane surface modifiers, e.g., phenylsilanes and trimethylsilyl group capping agents such as 1,1,1,3,3,3-hexamethyldisilazane. It has also been found that amine promoters can accelerate the surface-modification reaction with other silanes that are slow to react (e.g., phenyl silane, alkenyl silane, fluoroalkyl silane and combinations thereof).

It has been found that nanocomposites can be prepared from carboxylic acid-containing polymers and aminosilane-modified silica nanoparticles. The nanocomposites typically exhibit an increase in crystallization temperature and improved properties such loss modulus, storage modulus, creep resistance, and wear resistance, without sacrificing optical clarity. Clarity is typically reduced if the nanoparticles have agglomerated or if composites have been prepared from particles that are larger than nanoparticles.

Colloidal silica nanoparticle dispersions are commercially available as either an aqueous dispersion or as a dispersion in an organic solvent. The dispersions can also be prepared by methods known in the art. The colloidal silica nanoparticles of such dispersions typically have an average particle size of less than 75 nm, or less than 50 nm. Suitable dispersions comprise about 1 to about 70 wt %, or about 5 to about 50 wt %, or about 7 to about 30 wt % of colloidal silica nanoparticles, the balance being predominantly the aqueous or organic medium of the dispersion. Suitable organic solvents include alcohols (e.g., isopropanol, methanol), amides (e.g., dimethylacetamide, dimethylformamide) and ketones (e.g., 2-butanone).

Suitable silanes include silanes of Formula 1

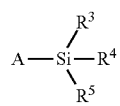

Formula 1 wherein
A is selected from the group consisting of alkyl groups, alkenyl groups, arylalkyl groups, alkoxyalkyl groups, alkoxyaryl groups, fluorine-substituted alkyl groups, aryl groups and N-aryl-substituted aminoalkyl groups;
$R^3$ is a $C_1$-$C_{10}$ alkoxy group; and
$R^4$ and $R^5$ are independently selected from the group consisting of $C_1$-$C_{10}$ alkyl and $C_1$-$C_{10}$ alkoxy groups.

Specific examples of suitable aminosilanes include N-phenylaminopropyltrimethoxysilane, and N-phenylaminopropyltriethoxysilane.

Aminosilanes of Formula 1 can be obtained from commercial sources or prepared by methods known in the art.

Suitable silanes also include phenyltrialkoxysilane (e.g., phenyltrimethoxysilane and phenyltriethoxysilane), alkyltrialkoxysilane (e.g., octyltrimethoxysilane, octyltriethoxysilane, methyltrimethoxysilane and methyltriethoxysilane), alkenyltrialkoxysilane (e.g., allyltrimethoxysilane, 3-butenyltriethoxysilane, 5-hexenyltriethoxysilane, 7-octenyltrimethoxysilane, and 10-undecenyltrimethoxysilane), fluoroalkyltrialkoxysilanes, perfluoroalkyl-alkyltrialkoxysilanes, and perfluoroalkylethyltrialkoxysilanes (e.g., nonafluoro-1,1,2,2-tetrahydrohexyltrimethoxysilane, tridecafluoro-1,1,2,2-tetrahydrooctyltrimethoxysilane, tridecafluoro-1,1,2,2-tetrahydrooctyltriethoxysilane, heptadecafluoro-1,1,2,2-tetrahydrodecyltrimethoxysilane).

In some embodiments, A comprises a terminal alkenyl group, e.g., $CH_2$=CH— or $CH_2$=C(Me)-.

To prepare the surface-modified silica nanoparticles, a silane is typically added to the colloidal silica nanoparticle dispersion in a molar amount equal to about 30% to about 50% of the accessible silanol groups estimated to be on the surface of the nanoparticles. Thus, the silane is typically added at a level of about 1.5 to about 4 molecules per square nanometer of silica surface area. The silica surface area can be determined by the BET (Brunauer, Emmet, Teller) method, for example using an adaptation of ASTM D1993-03 (2008) "Standard Test Method for Precipitated Silica-Surface Area by Multipoint BET Nitrogen Adsorption."

In some embodiments, the reaction mixture further comprises one or more other aminosilanes of Formula 1. In some embodiments, the reaction mixture comprises one or more other silanes. Suitable other silanes should not cause the colloidal silica nanoparticles to gel, agglomerate, or aggregate. Suitable other silanes include phenyltrimethoxysilane, octyltrimethoxysilane, 5-hexenyltriethoxysilane and tridecafluoro-1,1,2,2-tetrahydrooctyltrimethoxysilane.

In some embodiments, the reaction mixture comprises "sluggish" silanes that react slowly at temperatures below the boiling point of the solvent medium used for the reaction, and, in the absence of an amine promoter, may not achieve complete reaction, even after several hours.

The reaction mixture further comprises an amine promoter that allows the reaction to be run at a lower temperature and/or for a shorter time. These amine promoters can accelerate the surface modification of colloidal silica with or by the aromatic aminosilanes and other silanes that do not also contain amine functionality, without causing the silica nanoparticles to gel, agglomerate, or aggregate.

Amine promoters typically have a $pK_b$ less than about 7.0, or less than about 6.0, or less than about 5.0. For example, ethylamine, ethanolamine, propylamine (all isomers), butylamine (all isomers), hexylamine (all isomers), and decylamine (all isomers) each have a $pk_b$ of about 3.2-3.4, and the $pK_b$ of benzylamine is 4.7. These amines can serve as amine promoters.

Amine promoters typically have the structure $NR_3$, where each R is independently selected from the group of H, $C_1$-$C_{16}$ alkyl and substituted $C_1$-$C_{16}$ alkyl. Suitable substituents include ether, hydroxyl and aryl groups. In some embodiments, R is ethyl, isopropyl, n-propyl, n-butyl, isobutyl, cyclohexyl, 2-ethoxyethyl, 2-methoxyethyl, 2-hydroxyethyl or benzyl.

Suitable aliphatic amine promoters include primary alkyl amines (i.e. $NH_2R$, where R is alkyl), secondary alkyl amines (i.e., $NHR_2$, where R is alkyl), tertiary alkyl amines (i.e., $NR_3$, where R is alkyl) and arylalkylamines (e.g., phenylethyl, phenylpropyl, phenyl butyl), optionally substituted with ether, hydroxyl or polyether groups. In some embodiments, the amine promoter has a boiling point between 20-100° C. In some embodiments, the amine promoter is volatile enough to be easily removed from the colloid or from the polymer-silica nanocomposites at room temperature or with moderate heat, and generally has a boiling point of about 100° C. or below. In some embodiments, the amine promoter has a boiling point above 100° C.

The molar ratio of the amine promoter to silane surface-modifier is typically about 1:100 to about 3:1, or about 5:100 to 1:1.

In some embodiments, the process further comprises adding a trimethylsilyl group capping agent such as 1,1,1,3,3,3-hexamethyldisilazane (HMDS) to the reaction mixture. Such capping agents react with accessible silanol groups on the silica surface that have not been modified by the silanes and the optional other silanes. The capping agents are therefore most conveniently added after the reaction with the silanes has been carried out. The capping agent can be added at a level that is equivalent to the number of silanol groups that have not been modified by the silanes. Excess capping agent can also be used if it is volatile, and excess unreacted capping agent can be removed from the reaction mixture by evaporation or distillation. Alternatively, excess capping agent can be left in the reaction mixture containing the silane-modified silica nanoparticles and removed in later processing steps, e.g., during the preparation of nanocomposites, when the silica nanoparticles are combined with a polymer.

Use of capping agents allows one to fine-tune the amount of amine functionality, while still covering the surface with silanes to block accessible Si—OH groups that can cause particle aggregation. For example, $Me_3Si$ capping (via HMDS) removes essentially all accessible Si—OH sites that might cause particle aggregation. This can make it possible to dry the particles, and then redisperse them in a solvent to their original, small nanoparticle size, with few agglomerates or aggregates.

HMDS and silanes such as trimethylmethoxysilane, phenyldimethylmethoxysilane and octyldimethylmethoxysilane can be used as capping agents and can be obtained from commercial sources.

In some embodiments, the process further comprises heating the reaction mixture. For example, the silane can be added to the colloidal silica nanoparticles and amine promoter with agitation, followed by heating the mixture to the desired temperature, e.g., the boiling point of the solvent. The heating can be continued until a substantial portion of the silane has been reacted with the silica. The heating can be continuous or discontinuous. Typical total heating times can be from about 0.1 hour to 100 hours, or about 1 to 48 hours, or about 2 to 24 hours.

In some embodiments, the process further comprises an ultrasonic treatment step in which ultrasonic energy is delivered by an ultrasonic bath, probe, or other suitable source to break up any loose clusters or agglomerates of nanoparticles that may have formed during the surface modification process.

In some embodiments, the process further comprises isolating the silane-modified silica nanoparticles by evaporating water or the organic solvent at room temperature or by using gentle heating. However, severe heating may cause the nanoparticles to agglomerate or aggregate. In some embodiments, removal of water or organic solvent is carried out at reduced pressure.

In some embodiments, the process further comprises washing the silane-modified silica nanoparticles with a solvent selected from the group consisting of alcohols, aromatic solvents, ethers, and combinations thereof.

In some embodiments, the silane-modified silica nanoparticles can be isolated from the solvent, dried, and added to the polymer directly by a melt-blending process. In such a process, the particles are added to the molten polymer in a mixer such as an extruder, a Brabender PlastiCorder®, an Atlantic mixer, a Sigma mixer, a Banbury mixer, or 2-roll mill.

Alternatively, the isolated silane-modified silica nanoparticles can be mixed with a polymer in a compatible solvent. In this process, the silane-modified colloidal silica and the polymer are in the same solvent, or are in solvents that are miscible with each other. This process can afford nanocomposites in which the silica particles are well-dispersed within the host polymer after removal of the solvent, without a substantial number of agglomerates or aggregates of silica particles in the host polymer.

EXAMPLES

Materials for Examples and Comparative Examples

Colloidal silica was obtained from Nissan Chemical (Organosol® IPA-ST-MS, 30 wt % $SiO_2$ (17-23 nm diameter) in isopropyl alcohol) and from Gelest (Morrisville, Pa.; 31.5 wt % $SiO_2$ (16-20 nm) in isopropyl alcohol, #SIS6963.0). n-Propylamine (MW=59.1, bp 48° C., 98%, #109819); triethylamine (MW=101.19, by 88.8 C, 99.5%, #471283); ethanolamine (MW=61.08, by 170° C., 99.5%, #411000); N,N-diisopropylethylamine (MW=129.24, by 127° C., 99%, #550043); 1,1,1,3,3,3-hexamethyl disilazane (99.9%, #379212, bp=125° C., spgr=0.774, FW=161.4); and trimethoxyphenylsilane ($PhSi[OMe]_3$, FW=198.3, #435651, ≥94%, Dow Corning® product Z-6124) were obtained from Aldrich (St. Louis, Mo.). Dynasylan F8261 (tridecafluoro-1,1,2,2-tetrahydrooctyltriethoxysilane, 3 wt % TEOS, MW=510.4) was obtained from Evonik Industries.

The following trialkoxysilanes were supplied by Gelest (Morrisville, Pa.):
tridecafluoro-1,1,2,2-tetrahydrooctyltrimethoxysilane (MW=468.29, bp 60° C./0.5 torr, #SIT8176.0), heptadecafluoro-1,1,2,2-tetrahydrodecyltrimethoxysilane (MW=568.3, bp 247° C., #SIH5841.5), 5-hexenyltriethoxysilane (MW=246.43, bp 97° C./1 torr, #SIH6164.2), 7-octenyltrimethoxysilane (MW=232.39, bp 48° C./0.1 torr, #SIO6709.0) p-aminophenyltrimethoxysilane (MW=213.3, #SIA0599.1, 90%)

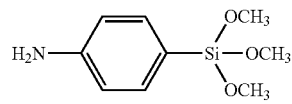

and
N-phenylaminopropyltrimethoxysilane (MW=255.38, # SIP6724.0, 95% d=1.07)

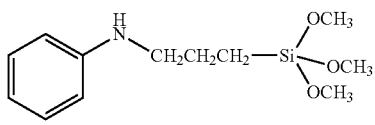

Dynamic light scattering was carded out with either a Zetasizer Nano-S (Malvern instruments) or a Brookhaven Instruments BI9000.

Examples 1-2 and Comparative Example A

Accelerating Effect of Propylamine Promoter with N-phenylaminopropyltrimethoxysilane These examples demonstrate that the surface modification of colloidal $SiO_2$ with sluggish silanes like the aromatic aminosilane, can be accelerated and improved by the use of an amine promoter, without adverse effect on particle size and agglomeration.

Colloidal $SiO_2$ (25.0 g) was added to each of three 3-neck round-bottomed flasks (250 ml for Comparative Example A and 500 mL for Examples 1 and 2) and diluted with isopropyl alcohol (50 g). To each flask, a stirring bar was added and a water-cooled condenser attached with a drying tube atop it. Rapid stirring was begun at room temperature. N-Phenylaminopropyltrimethoxysilane (0.77 g) was added via needle and syringe at room temperature to each of the three flasks; n-propylamine (0.18 g) was also added to the flasks for Examples 1 and 2. The mixtures became hazy in appearance. The mixtures were heated and remained hazy, without a viscosity increase. Over a 3-day period, mixture (Example 1) was held at reflux for 24 hours, then cooled to room temperature, while mixture 2 (Example 2) was simply held at room temperature for 24 hours. Over a 3-day period, the mixture for Comparative Example A was refluxed for 23 hr, then cooled to room temperature. Then 1,1,1,3,3,3-hexamethyldisilazene (2.6 g) was added, the mixture held at room temperature for 4 hr, heated to reflux for 4 hr, and then cooled to room temperature. None of the mixtures was gelled at room temperature.

The reaction mixtures were diluted with isopropanol to 0.24 wt % solids and then sonicated with a bath sonicator, and submitted for particle size analysis, along with a sample of untreated colloidal silica. A 20.0-g portion of each diluted reaction mixture was allowed to evaporate slowly in an evaporating dish overnight, yielding 2.0 to 2.2 g of solid. A 0.5-g portion of each solid was ground to a powdery state and cleaned up by washing on a vacuum filter successively with two portions each of isopropanol, toluene, and tetrahydrofuran, in that order. During each wash, the solid was slurried for a short time with the solvent before pulling vacuum. The solids were dried. Both sets of solids, before and after the washing, were air-dried, then dried in a vacuum oven overnight at 50° C. with a slight nitrogen bleed, and then submitted for elemental analysis.

Analysis of the dried solids by dynamic light scattering in a Brookhaven Instruments BI9000 showed that the effective diameters (which are most sensitive to the largest particles in the colloids) and polydispersities (breadth of the particle size distributions) are substantially the same as, or less than, those of untreated colloidal silica (36 nm and 0.30 nm, respectively), indicating that agglomeration had not occurred to a significant extent.

Analysis of the unwashed solids shows that N-phenylaminopropyltrimethoxysilane was added to the surface of the $SiO_2$ particles for Comparative Example A and for Examples 1 and 2. As shown by the % N from the microanalysis of the treated particles in Table 1, amine is present on the dried $SiO_2$ particles, in an amount that would be expected if all of the aminosilane had attached to the surface of the $SiO_2$. Also, the % C, % H, and % N data shown in Table 1 indicate that most of the aminosilane on the particle surface is retained for Examples 1 and 2, even after washing of the particles with copious amounts of solvent. In contrast, for Comparative A, which was prepared without the use of an amine promoter, approximately half of the aminosilane was lost on washing. This better attachment of the aminosilane for samples prepared in the presence of an amine promoter was observed even for Example 2, which was prepared at room temperature. The amine promoter does not cause agglomeration or an increase in particle size.

TABLE 1

Analytical data for Comparative Example A and Examples 1-2

| | Examples | | |
|---|---|---|---|
| | A (Comparative) | 1 | 2 |
| Particle size, effective diameter, nm, (90° scattering angle) | 25 | 23 | 28 |
| Polydispersity, (90° scattering angle) | 0.28 | 0.25 | 0.27 |
| % C, H, N (microanalysis) before washing | 7.3/1.26/0.50 | 5.2/0.82/0.54 | 4.8/0.74/0.56 |
| Expected % N if all of amino silane is added | 0.51 | 0.51 | 0.51 |
| % C, H, N (microanalysis) after washing | 3.4/0.68/0.22 | 4.6/0.74/0.48 | 4.6/0.72/0.54 |
| % retention of C/H/N after washing | 47/53/44 | 89/90/88 | 95/97/96 |

Examples 3 and 4

Accelerating Effect of Propylamine Promoter with Trimethoxyphenylsilane Surface Treatment These examples demonstrate that the surface modification of colloidal $SiO_2$ with sluggish silanes, like trimethoxyphenylsilane, that do not possess internal catalytic moieties can be accelerated and improved by the use of an amine promoter, without adverse effect on particle size and agglomeration.

Colloidal $SiO_2$ (25.0 g) was added to each of two 250 ml, 3-neck round-bottomed flasks and diluted with isopropyl alcohol (50 g). To each flask, a stirring bar was added and a water-cooled condenser attached with a drying tube atop it. Rapid stirring was begun at room temperature. Trimethoxyphenylsilane (0.74 g) and n-propylamine (0.22 g) were added via needle and syringe at room temperature to the flask, making the mixtures hazy in appearance. The mixtures were heated and remained hazy, without a viscosity increase. Over a 2-day period, mixture 3 (Example 3) was held at reflux for 16 hours, then cooled to room temperature; mixture 4 (Example 4) was held at room temperature for 24 hours. Neither of these mixtures gelled at room temperature.

The reaction mixtures were diluted with isopropanol to 0.24 wt % solids, sonicated with a bath sonicator, and then submitted for particle size analysis. A 20.0-g portion of each reaction mixture was allowed to evaporate slowly in an evaporating dish overnight, yielding 2.2 to 2.5 g of solid. A 0.5-g portion of each solid was ground to a powdery state and cleaned up by washing on a vacuum filter successively with two portions each of isopropanol, toluene, and tetrahydrofuran, in that order. During each wash, the solid was slurried for a short time with the solvent before pulling vacuum. Both sets of solids, before and after the washing, were air-dried, then dried in a vacuum oven overnight at 50° C. with a slight nitrogen bleed, and then submitted for elemental analysis.

Analysis of the dried solids by dynamic light scattering in a Brookhaven Instruments BI9000 showed that the effective diameters (which are most sensitive to the largest particles in the colloids) and polydispersities (breadth of the particle size distributions) are less than those of untreated colloidal silica (36 nm and 0.30, respectively), indicating that agglomeration has not occurred to a significant extent.

As shown by the % C from the microanalysis of the treated particles in Table 2, carbon is present on the dried $SiO_2$ particles, in an amount comparable to what would be expected if all of the silane had attached to the surface of the $SiO_2$. As shown by the changes in % C and % H in the microanalysis, much of the silane on the particle surface is retained even after washing the particles with copious amounts of solvent. This good attachment is also observed for the product of Example 4, that was prepared at a much lower temperature (i.e., room temperature). The amine promoter does not cause agglomeration that would increase the particle size.

TABLE 2

Analytical data for Examples 3 and 4

|  | Examples | |
|---|---|---|
|  | 3 | 4 |
| Particle size, effective diameter, nm | 28 | 27 |
| Polydispersity | 0.18 | 0.18 |
| % C, H, N (microanalysis) before washing | 4.8/0.66/0.07 | 4.3/0.60/0.10 |
| Expected % C if all of silane is added, without hydrolysis of unreacted $OCH_3$ | 4.9 | 4.9 |
| Expected % C if all of silane is added, with hydrolysis of unreacted $OCH_3$ | 3.3 | 3.3 |
| % C, H, N (microanalysis) after washing | 3.8/0.58/0.05 | 3.5/0.49/0.08 |
| % retention of C/H after washing | 80/89 | 80/82 |

Examples 5-7

Accelerating Effect of Aliphatic Amine Promoter on Surface-Treatment with Non-Self-Catalytic Perfluoroalkyl-Alkyl Silane and Optional Hexamethyl Disilazane Secondary Surface Modifier These examples demonstrate that the surface modification of colloidal $SiO_2$ with sluggish fluoroalkyl silanes that do not possess internal catalytic moieties can be accelerated and improved by the use of an amine promoter, without adverse effect on particle size and agglomeration.

Colloidal $SiO_2$ (25.0 g) was added to each of three 250 ml, 3-neck round-bottomed flasks and diluted with isopropyl alcohol (50 g). To each flask, a stirring bar was added and a water-cooled condenser attached with a drying tube atop it. Rapid stirring was begun at room temperature. Tridecafluoro-1,1,2,2-tetrahydrooctyltriethoxysilane (1.90 g) and n-propylamine (0.22 g) were added via needle and syringe at room temperature to flasks, making the mixture hazy in appearance. The mixtures were heated with a heating mantle and remained hazy, without a viscosity increase. Over a 2-day period, mixtures 5 (Example 5) and 7 (Example 7) were held at reflux for 16 hr, then cooled to room temperature. Mixture 6 (Example 6) was simply held at room temperature. Mixture 7 (Example 7) was then treated with 2.4 g of 1,1,1,3,3,3-hexamethyldisilazane and held at room temperature for 4 hr and then refluxed for 4 hr.

The reaction mixtures were diluted with isopropanol to 0.24 wt % solids, sonicated with a bath sonicator, and then submitted for particle size analysis. A 20.0-g portion of each was allowed to evaporate slowly in an evaporating dish overnight, yielding 2.3 to 2.5 g of solid. A 0.5-g portion of each solid was ground to a powdery state and cleaned up by washing on a vacuum filter successively with two portions each of isopropanol, toluene, and tetrahydrofuran, in that order. During each wash, the solid was slurried for a short time with the solvent before pulling vacuum. The solids, before and after the washing, were air-dried, then dried in a vacuum oven overnight at 50° C. with a slight nitrogen bleed, and then submitted for elemental analysis.

Analysis of the dried solids by dynamic light scattering in a Brookhaven Instruments BI9000 shows that the effective diameters (which are most sensitive to the largest particles in the colloids) and polydispersities (breadth of the particle size distributions) are less than those of untreated colloidal silica (36 nm and 0.30, respectively), indicating that agglomeration has not occurred to a significant extent.

As shown by the % C from the microanalysis of the treated particles in Table 3, carbon is present on the dried $SiO_2$ particles, in an amount that would be expected if all of the tridecafluoro-1,1,2,2-tetrahydrooctyltriethoxysilane had attached to the surface of the $SiO_2$ and been fully hydrolyzed. As shown by the % F from the microanalysis of the treated particles, fluorine is present on the dried $SiO_2$ particles, about 60% of what would be expected if all of the silane had attached to the surface of the $SiO_2$.

As shown by the changes in % C, H, and F in the microanalysis in the table after washing the particles treated with this silanes, much of the silane on the particle surface is retained after washing of the particles. This good attachment is even true for the Example 6, which was prepared at room temperature. The amine promoter does not cause agglomeration or an increase in particle size. The 1,1,1,3,3,3-hexamethyldisilazane does not also interfere.

TABLE 3

Analytical data for Examples 5-7

|  | Examples | | |
|---|---|---|---|
|  | 5 | 6 | 7 |
| Particle size, effective diameter, nm | 20 | 21 | 20 |
| Polydispersity | 0.18 | 0.16 | 0.18 |
| % C, H, F (microanalysis) before washing | 3.3/0.46/6.0 | 2.9/0.44/— | 3.3/0.50/— |
| Expected % F if all of silane is added, regardless of hydrolysis of unreacted $OCH_3$* | 9.8 | 9.8 | 9.8 |
| Expected % C if all of silane is added, without hydrolysis of unreacted $OCH_3$* | 6.7 | 6.7 | 6.7 |
| Expected % C if all of silane is added, with hydrolysis of unreacted $OCH_3$* | 3.8 | 3.8 | 3.8 |
| % C, H, F (microanalysis) after washing | 3.2/0.46/5.5 | 2.8/0.44/— | 3.2/0.48/— |
| % retention of C/H after washing | 98/99 | 95/102 | 97/98 |

*Does not reflect the contribution of HMDS surface modification

Comparative Example B

Effect of heptadecafluoro-1,1,2,2-tetrahydrodecyltrimethoxy Silane Surface Treatment without any Promoter The following example demonstrates the poor ligand attachment of a sluggish fluoroalkyl silane, that does not possess internal catalytic moieties, to colloidal silica when no promoter is added to the reaction.

A 500 ml 3-necked jacketed flask, equipped with reflux condenser and mechanical paddle stirrer, was charged with Gelest SiO$_2$/IPA (63.5 g), heptadecafluoro-1,1,2,2-tetrahydrodecyltrimethoxy silane (5.03 g) and isopropyl alcohol (70 g). With gentle stirring, the reaction mixture was heated to 80° C. for 24 hr then cooled to ambient temperature. The reaction remained fluid and clear.

One half of the reaction mixture was gently evaporated to dryness under vacuum at 20° C. yielding 12.1 g of granular solid. The solid was analyzed for organic ligand content by determining the percent weight loss after thermogravimetric ashing of the sample in air. It was determined the sample contained 17.1 wt % organic ligand after evaporation.

A 2.0 g sample of the granular solid above was washed 3× in tetrahydrofuran and then 3× in toluene. For each wash, the solids were suspended and agitated in 35-40 ml of solvent then centrifuged at 3300 rpm to separate the solids from the solvent. The supernatant was then decanted and the next wash was conducted. After the last wash, the solids were dried under reduced pressure at ambient temperature for 18 hr. The washed solid was analyzed for organic ligand content by determining the percent weight loss after thermogravimetric ashing of the sample in air. It was determined the washed sample contained only 8.6 wt % organic ligand. Thus, without any promoter only 50.3% of the organic ligand was attached to the colloidal silica and 49.7% of the organic ligand was unattached and was removed by washing.

Example 8

Accelerating Effect of Propylamine Promoter with heptadecafluoro-1,1,2,2-tetrahydrodecyltrimethoxy Silane Surface Treatment The following example demonstrates the near complete ligand attachment of a sluggish fluoroalkyl silane, that does not possess internal catalytic moieties, to colloidal silica when an amine promoter is added to the reaction, without adverse effect on particle size and agglomeration.

A 500 ml 3-necked jacketed flask, equipped with reflux condenser and mechanical paddle stirrer, was charged with Gelest SiO$_2$/IPA (63.5 g) and isopropyl alcohol (150 g). Separately, heptadecafluoro-1,1,2,2-tetrahydrodecyltrimethoxy silane (5.03 g) diluted with 20 g isopropyl alcohol and n-propylamine (0.25 g) diluted with 20 g isopropyl alcohol, were added to the flask in that order. With gentle stirring at ambient temperature, the reaction mixture gradually became cloudy, it was allowed to stir at ambient temperature for 18 hr followed by heating to 50° C. for 1 hr then 80° C. for 1 hr before cooling to ambient temperature. The reaction remained fluid and cloudy after cooling.

One half of the reaction mixture was gently evaporated to dryness under vacuum at 20° C. yielding 12.3 g of granular solid (8a). The solid was analyzed for organic ligand content by determining the percent weight loss after thermogravimetric ashing of the sample in air. It was determined the sample contained 20.6 wt % organic ligand after evaporation.

A 2.0 g sample of the granular solid, 8a, was washed 3× in tetrahydrofuran and then 3× in toluene. For each wash, the solids were suspended and agitated in 35-40 ml of solvent then centrifuged at 3300 rpm to separate the solids from the solvent. The supernatant was then decanted and the next wash was conducted. After the last wash, the solids were dried under reduced pressure at ambient temperature for 18 hr. The washed solid was analyzed for organic ligand content by determining the percent weight loss after thermogravimetric ashing of the sample in air. It was determined the washed sample contained 20.1 wt % organic ligand. Thus, the use of an amine promoter resulted in 97.6% of the organic ligand being attached to the colloidal silica and only 2.4% of the organic ligand was unattached and was removed by washing.

A 500 ml 3-necked flask, equipped with reflux condenser, nitrogen inlet and mechanical paddle stirrer, was charged with the granular solid, 8a (9.94 g) and propyl acetate (150 g). With gentle stirring of the 8a/propyl acetate slurry, the flask was flushed with nitrogen and submerged in an ultrasonic bath. The ultrasonic bath was energized and 1,1,1,3,3,3-hexamethyldisilazane (2.5 g, 25 pph vs. 8a) was injected. The ultrasonic bath was allowed to heat to 45° C. After several hours the slurry became translucent and homogeneous in appearance. The reaction was allowed to proceed for 24 hr after which time it was cooled to ambient temperature and evaporated to dryness under reduced pressure at ambient temperature to yield 10.0 g of granular solid (8b).

A 0.25 wt % colloidal dispersion of 8b was prepared in 2,3-dihydroperfluoropentane by combining the two in a 15 ml centrifuge tube and subjecting the mixture to ultrasonic agitation. Analysis of the colloidal dispersion by dynamic light scattering in a Brookhaven Instruments BI9000 shows that the effective diameter (which is most sensitive to the largest particles in the colloidal dispersion) is equal to 21.8 nm which is nearly equal to that of the untreated colloidal silica (16-20 nm) indicating that agglomeration of the particles has not occurred to a significant extent.

Examples 9-12

Accelerating Effect of Amine Promoters with heptadecafluoro-1,1,2,2-tetrahydrodecyltrimethoxy Silane Surface Treatment The following examples further exemplify the near complete ligand attachment of a sluggish fluoroalkyl silane, that does not possess internal catalytic moieties, to colloidal silica when an amine promoter is added to the reaction, without adverse effect on particle size and agglomeration. The following examples demonstrate the range of amine promoters that can be used in this invention.

For Examples 9-12, the procedure of Example 8 was repeated with the following exception: the chemical nature of the amine promoter was changed. The analytical data is tabulated in Table 4 below along with the analytical data for Example 8 and Comparative Example B.

TABLE 4

Analytical data for Comparative Example B and Examples 8-12

| Example | Promoter | Ligand content after evaporation (a) | Ligand content after washing (b) | % Ligand attached | Effective particle diameter in DHPFP |
|---|---|---|---|---|---|
| B | none | 17.1 wt % | 8.6 wt % | 50.3% | |
| 8 | n-PrNH$_2$ (0.25 g) | 20.6 wt % | 20.1 wt % | 97.6% | 21.8 nm |

TABLE 4-continued

Analytical data for Comparative Example B and Examples 8-12

| Example | Promoter | Ligand content after evaporation (a) | Ligand content after washing (b) | % Ligand attached | Effective particle diameter in DHPFP |
|---|---|---|---|---|---|
| 9 | n-PrNH$_2$ (0.25 g) water (2.4 g) | 20.7 wt % | 20.6 wt % | 99.5% | 19.8 nm |
| 10 | Et$_3$N (0.43 g) water (2.4 g) | 19.6 wt % | 19.65 wt % | 100% | 22.0 nm |
| 11 | i-Pr$_2$NEt (0.55 g) water (2.45 g) | 19.9 wt % | 19.6 wt % | 98.5% | 19.1 nm |
| 12 | HO—Et—NH$_2$ (0.25 g) water (2.4 g) | 20.8 wt % | 20.2 wt % | 97.1% | 24.6 nm | n-PrNH$_2$ = n-propylamine;
Et$_3$N = triethylamine;
i-Pr$_2$NEt = di-isopropylethylamine;
HO—Et—NH$_2$ = 2-hydroxyethylamine;
DHPFP = 2,3-dihydroperfluoropentane Example 13

Accelerating Effect of Propylamine Promoter with 7-octenyltrimethoxysilane Surface Treatment The following example demonstrates the near complete ligand attachment of a sluggish 1-alkene silane, that does not possess internal catalytic moieties, to colloidal silica when an amine promoter is added to the reaction, without adverse effect on particle size and agglomeration.

A 500 ml 3-necked jacketed flask, equipped with reflux condenser and mechanical paddle stirrer, was charged with Gelest SiO$_2$/IPA (79.5 g), isopropyl alcohol (130 g), distilled water (2.64 g) and 7-octenyltrimethoxysilane (2.27 g). Separately, n-propylamine (0.32 g) diluted with 20 g isopropyl alcohol was added to the flask with gentle stirring at ambient temperature. The reaction mixture was heated to 50° C. for 1 hr then 80° C. for 18 hr before cooling to ambient temperature. The reaction mixture was fluid and clear after cooling.

The reaction mixture was gently evaporated to dryness under vacuum at 20° C. yielding 25.4 g of granular solid (13a). The solid was analyzed for organic ligand content by determining the percent weight loss after thermogravimetric ashing of the sample in air. It was determined the sample contained 6.35 wt % organic ligand after evaporation.

A 1.0 g sample of the granular solid, 13a, was washed 1× in propylacetate and then 4× in toluene. For each wash, the solids were suspended and agitated in 35-40 ml of solvent then centrifuged at 3300 rpm to separate the solids from the solvent. The supernatant was then decanted and the next wash was conducted. After the last wash, the solids were dried under reduced pressure at ambient temperature for 18 hr. The washed solid was analyzed for organic ligand content by determining the percent weight loss after thermogravimetric ashing of the sample in air. It was determined the washed sample contained 6.1 wt % organic ligand. Thus, the use of an amine promoter resulted in 96.1% of the organic ligand being attached to the colloidal silica and only 3.9% of the organic ligand was unattached and was removed by washing.

A 500 ml 3-necked flask, equipped with reflux condenser, nitrogen inlet and mechanical paddle stirrer, was charged with the granular solid, 13a (23.2 g) and propyl acetate (300 g). With gentle stirring of the 13a/propyl acetate slurry, the flask was flushed with nitrogen and submerged in an ultrasonic bath. The ultrasonic bath was energized and 1,1,1,3,3,3-hexamethyldisilazane (5.8 g, 25 pph vs. 13a) was injected.

The ultrasonic bath was allowed to heat to 45° C. After several hours the slurry became translucent and homogeneous in appearance. The reaction was allowed to proceed for 24 hr after which time it was completely clear. The reaction mixture was cooled to ambient temperature and evaporated to dryness under reduced pressure at ambient temperature to yield 24.0 g of granular solid (13b).

A 0.25 wt % colloidal dispersion of 13b was prepared in isopropyl alcohol by combining the two in a 15 ml centrifuge tube and subjecting the mixture to ultrasonic agitation. Analysis of the colloidal dispersion by dynamic light scattering in a Brookhaven Instruments BI9000 shows that the effective diameter (which is most sensitive to the largest particles in the colloidal dispersion) is equal to 17.7 nm which is nearly equal to that of the untreated colloidal silica (16-20 nm) indicating that agglomeration of the particles has not occurred to a significant extent.

Example 14

Accelerating Effect of Propylamine Promoter with a Combination of 5-hexenyltriethoxysilane and tridecafluoro-1,1,2,2-tetrahydroocyltrimethoxy Silane Surface Treatment The following example demonstrates the near complete ligand attachment of a combination of a sluggish alkene silane and a sluggish fluoroalkyl silane that do not possess internal catalytic moieties, to colloidal silica when an amine promoter is added to the reaction, without adverse effect on particle size and agglomeration.

A 1000 ml 3-necked jacketed flask, equipped with reflux condenser and mechanical paddle stirrer, was charged with Gelest SiO$_2$/IPA (160 g), isopropyl alcohol (260 g), distilled water (6.92 g), 5-hexenyltriethoxysilane (0.82 g) and tridecafluoro-1,1,2,2-tetrahydroocyltrimethoxy silane (10.44 g). Separately, n-propylamine (0.64 g) diluted with 40 g isopropyl alcohol was added to the flask with gentle stirring at ambient temperature. The reaction mixture was allowed to stir at ambient temperature for 2 hr and gradually became cloudy then was heated to 50° C. for 1 hr then 80° C. for 18 hr before cooling to ambient temperature. After cooling the reaction mixture was fluid and slightly cloudy.

The reaction mixture was gently evaporated to dryness under vacuum at 20° C. yielding 58.4 g of granular solid (14a). The solid was analyzed for organic ligand content by determining the percent weight loss after thermogravimetric ashing of the sample in air. It was determined the sample contained 16.85 wt % organic ligand after evaporation.

A 1.0 g sample of the granular solid, 14a, was washed 4× in toluene. For each wash, the solids were suspended and agitated in 35-40 ml of solvent then centrifuged at 3300 rpm to separate the solids from the solvent. The supernatant was then decanted and the next wash was conducted. After the last wash, the solids were dried under reduced pressure at ambient temperature for 18 hr. The washed solid was analyzed for organic ligand content by determining the percent weight loss after thermogravimetric ashing of the sample in air. It was determined the washed sample contained 16.36 wt % organic ligand. Thus, the use of an amine promoter resulted in 97.1% of the organic ligands being attached to the colloidal silica and only 2.9% of the organic ligands were unattached and were removed by washing.

A 1000 ml 3-necked flask, equipped with reflux condenser, nitrogen inlet and mechanical paddle stirrer, was charged with the granular solid, 14a (56.7 g) and propyl acetate (300 g). With gentle stirring of the 14a/propyl acetate slurry, the flask was flushed with nitrogen and submerged in an ultrasonic bath. The ultrasonic bath was energized and 1,1,1,3,3,3-hexamethyldisilazane (14.2 g, 25 pph vs. 14a) was injected. The reaction was allowed to heat to 45° C. The reaction was allowed to proceed for 24 hr after which time it was cooled to ambient temperature and evaporated to dryness under reduced pressure at ambient temperature to yield 57.7 g of granular solid (14b).

A 0.25 wt % colloidal dispersion of 14b was prepared in 2,3-dihydroperfluoropentane by combining the two in a 50 ml centrifuge tube and subjecting the mixture to ultrasonic agitation. Analysis of the colloidal dispersion by dynamic light scattering in a Brookhaven Instruments BI9000 shows that the effective diameter (which is most sensitive to the largest particles in the colloidal dispersion) is equal to 20.1 nm which is nearly equal to that of the untreated colloidal silica (16-20 nm) indicating that agglomeration of the particles has not occurred to a significant extent.

What is claimed is:

1. A process comprising forming a reaction mixture comprising:
   a) a dispersion of colloidal silica nanoparticles in a non-aqueous organic solvent, the nanoparticles having an average diameter of less than 75 nm;
   b) a silane of Formula 1:

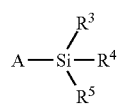

Formula 1 wherein
A is selected from the group consisting of alkyl groups, alkenyl groups, arylalkyl groups, alkoxyalkyl groups, alkoxyaryl groups, fluorine-substituted alkyl groups, aryl groups and N-aryl-substituted aminoalkyl groups;
$R^3$ is a $C_1$-$C_{10}$ alkoxy group; and
$R^4$ and $R^5$ are independently selected from the group consisting of $C_1$-$C_{10}$ alkyl and $C_1$-$C_{10}$ alkoxy groups; and
   c) an amine promoter having a $pK_b$ less than about 7.0.

2. The process of claim 1, wherein A is a phenyl group, a terminal alkenyl group, a fluorine-substituted alkyl group, or an N-phenylamino alkyl group.

3. The process of claim 1, wherein the amine promoter is a compound of formula $NR_3$, wherein each R is independently selected from the group of H, $C_1$-$C_{16}$ alkyl and substituted $C_1$-$C_{16}$ alkyl.

4. The process of claim 3, wherein R is ethyl, isopropyl, n-propyl, n-butyl, isobutyl, cyclohexyl, 2-ethoxyethyl, 2-methoxyethyl, 2-hydroxyethyl or benzyl.

5. The process of claim 1, wherein $R^3$, $R^4$, and $R^5$ are independently selected from methoxy and ethoxy groups.

6. The process of claim 1, further comprising isolating silane-modified silica nanoparticles from the reaction mixture.

7. The process of claim 6, further comprising washing the silane-modified silica nanoparticles with a solvent selected from the group consisting of alcohols, aromatic solvents, ethers, and combinations thereof.

8. The process of claim 1, wherein the amine promoter is selected from the group consisting of: n-propylamine, n-butylamine, ethanolamine, diethylamine, triethylamine, triethanolamine, hexylamine, cyclohexylamine, diisopropylamine, diisopropylethylamine, benzylamine, and 4-dimethylaminopyridine.

9. The process of claim 1, wherein the amine promoter has a boiling point between 20° C. and 100° C.

10. The process of claim 1, wherein the amine promoter is n-propylamine.

11. The process of claim 1, wherein the amine promoter is triethylamine.

12. The process of claim 1, wherein the amine promoter has a boiling point between 100° C. and 180° C.

13. The process of claim 1, wherein the amine promoter is diisopropylethylamine.

14. The process of claim 1, wherein the amine promoter is ethanolamine.

* * * * *